United States Patent
Lee et al.

(10) Patent No.: US 9,783,837 B2
(45) Date of Patent: Oct. 10, 2017

(54) CATECHOLAMINE-BASED VERSATILITY FILM AND A PREPARATION METHOD THEREOF

(71) Applicant: KOREA ADVANCED INSTITUTE OF SCIENCE AND TECHNOLOGY, Daejeon (KR)

(72) Inventors: Hae Shin Lee, Daejeon (KR); Seon Ki Hong, Daejeon (KR); Joseph Paul Park, Daejeon (KR)

(73) Assignee: Korea Advanced Institute of Science of Technology (KR)

( * ) Notice: Subject to any disclaimer, the term of this patent is extended or adjusted under 35 U.S.C. 154(b) by 0 days.

(21) Appl. No.: 14/735,456

(22) Filed: Jun. 10, 2015

(65) Prior Publication Data

US 2015/0361218 A1     Dec. 17, 2015

(30) Foreign Application Priority Data

Jun. 17, 2014    (KR) .................. 10-2014-0073386

(51) Int. Cl.
    *C12P 13/00*      (2006.01)
    *C08J 5/18*      (2006.01)
    *C08K 3/08*      (2006.01)
    *C08L 79/02*      (2006.01)
    *C12P 13/02*      (2006.01)
    *C12P 19/26*      (2006.01)

(52) U.S. Cl.
CPC .............. *C12P 13/001* (2013.01); *C08J 5/18* (2013.01); *C08K 3/08* (2013.01); *C08L 79/02* (2013.01); *C12P 13/02* (2013.01); *C12P 19/26* (2013.01); *C08J 2379/02* (2013.01); *C08K 2003/0806* (2013.01); *C08K 2201/013* (2013.01)

(58) Field of Classification Search
CPC .. C08G 73/02; C08K 3/08; C08K 2003/0806; C08K 2201/013; C12P 13/001; C12P 13/02; C12P 19/26; C08L 79/02; C08J 5/18; C08J 2379/02
USPC ......................................................... 524/440
See application file for complete search history.

(56) References Cited

U.S. PATENT DOCUMENTS 7,622,533 B2 * 11/2009 Lee .................. C08G 65/33389
                                           525/328.2

FOREIGN PATENT DOCUMENTS

KR    10-2013-0033996      4/2013
KR    10-2013-0055847      5/2013

OTHER PUBLICATIONS

B. P. Lee , P. B. Messersmith , J. N. Israelachvili , J. H. waite, "Mussel-Inspired Adhesives and Coatings", Annu. Rev. Mater. Res. 2011, 41, 99.
J. D. Simon, D. Peles , K. Wakamatsu , S. Ito, "Current challenges in understanding melanogenesis: bridging chemistry, biological control, morphology,and function", Pigment Cell Melanoma Res. 2009, 22 , 563.
H. Lee, S. M. Dellatore, W. M. Miller, P. B. Messersmith, "Mussel-Inspired Surface Chemistry for Multifunctional Coatings", Science 2007, 318, 426.
Seonki Hong , Clemens F. Schaber , Kirstin Dening , Esther Appel , Stanislav N. Gorb, and Haeshin Lee, "Air/Water Interfacial Formation of Freestanding, Stimuli-Responsive, Self-Healing CatecholamineJanus-Faced Microfi lms", Adv. Mater. 2014, 26, 7581-7587.

* cited by examiner

*Primary Examiner* — Ling Choi
*Assistant Examiner* — Ronald Grinsted
(74) *Attorney, Agent, or Firm* — Sheridan Ross, P.C.

(57) ABSTRACT

The present invention relates to a method for preparing a double-sided film containing the step of 5 forming a film in the interface between air and the mixture of a polymer comprising amine group (—NH) and a compound containing phenol or catechol by exposing the mixture on the air. Particularly, the double-sided film of the present invention is a separation membrane 10 that can separate the interface of liquid phase and gas phase and at the same time can be used as a biomaterial such as a haemostatic and also an waterproof agent. When the film is prepared in a moderate condition by using an enzyme, the film can include proteins and 15 cells, resulting in the multi-functional versatility film that can be useful as a biocatalyst. The versatility film of the present invention, thus, is not expensive and the production method thereof is simple and eco-friendly.

13 Claims, 13 Drawing Sheets

Fig.1
| | Pyrogallol | Dopamine | Pyrocatechol |
|---|---|---|---|
| 1 min | 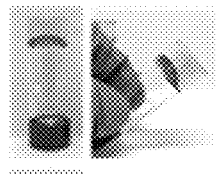 |  | 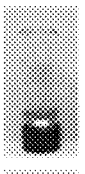 |
| 5 min | 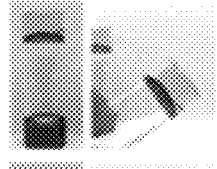 | 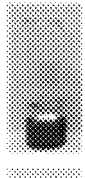 |  |
| 10 min | 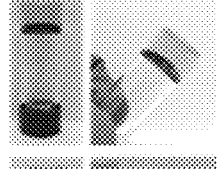 | 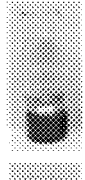 | 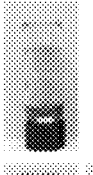 |
| 30 min |  | 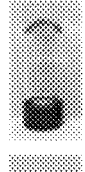 | 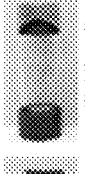 |
| 1 hr | 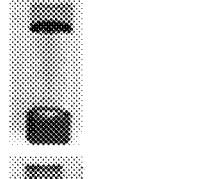 | 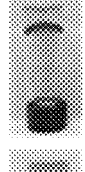 |  |
| 2 hr |  |  | 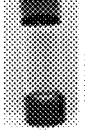 |
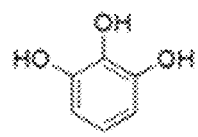
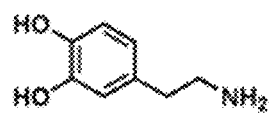
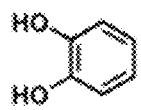

Fig. 12
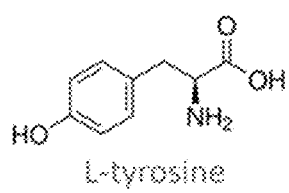
L-tyrosine
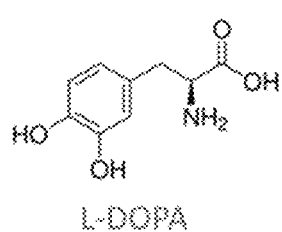
L-DOPA
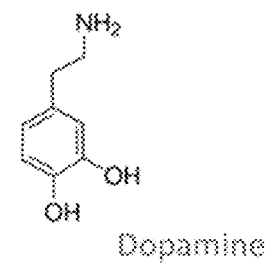
Dopamine
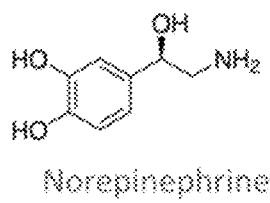
Norepinephrine
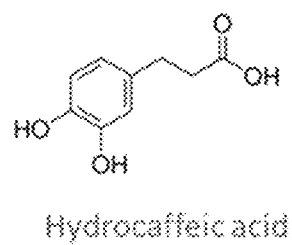
Hydrocaffeic acid
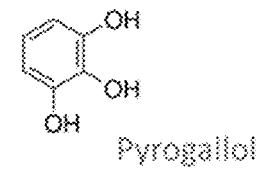
Pyrogallol

CATECHOLAMINE-BASED VERSATILITY FILM AND A PREPARATION METHOD THEREOF

BACKGROUND OF THE INVENTION

1. Field of the Invention

The present invention relates to a method for preparing a double-sided film containing the step of forming a film in the interface between air and the mixture of a polymer comprising amine group (—NH) and a compound containing phenol or catechol by exposing the mixture on the air.

2. Description of the Related Art

Catecholamines are found ubiquitously in nature. Wetting-resistant, adhesive foot-pads in mussels, neurotransmitters in the brain, melanin bio-pigments in the skin and eyes, squid beaks, and insect cuticles are related examples. In materials science, catecholamines have recently attracted significant attention due to the unprecedented material-independent surface-functionalization properties found in poly(dopamine) (pDA) and poly(norepinephrine). Another important aspect of catecholamines is their participation in catecholquinone-mediated oxidative crosslinking between bio-macromolecules such as polysaccharides and proteins. This biochemistry is the key factor in forming load-bearing, fully organic biomaterials tolerating wear and abrasion during the lifetime of the organism. This chemistry has been widely used to fabricate mechanically strong organic thin films and fibers and to prepare catecholamine-containing hydrogels. Both the achievement of the mechanical properties of pure organic materials similar to or better than those exhibited in inorganic materials, and the precise control of the mechanical properties of polymeric hydrogels are the aims of using catecholamine chemistry. Up to now, as mentioned above, catecholamine research has focused on either controlling the bulk material properties or functionalizing solid-liquid interfaces. However, another important, yet missing domain, the air-water interface, has long been overlooked in catecholamine material science.

The present inventors developed a film that is formed specifically in the interface between air and water by using a macromolecule containing a high amount of amine group (—NH) and a low molecular compound containing phenol or catechol. The present invention describes the interface specific characteristics of catecholamine chemical reaction for the first time. The prepared film is a double-sided film wherein the upper face and the lower face are different from each other. The film of the invention displays catecholamine specific adhesiveness and strong mechanical strength. When there is a mechanical damage on the film, the film can be auto-repaired and thus a new film membrane can be formed. At this time, an additional process can make the film multi-functional. When the film is produced with an enzyme that can oxidize catechol group by using air in a moderate condition, the film can harbor proteins and cells, so that it can be used as a biomaterial such as a haemostatic and also an industrial waterproof agent, making the film multi-purpose or multi-functional. The versatility film of the present invention, thus, is not expensive and the production method thereof is simple and eco-friendly. Therefore, the film of the invention has a high added-value as a novel separation membrane that can replace the conventional separation membrane.

SUMMARY OF THE INVENTION

It is an object of the present invention to provide a method for preparing a double-sided film containing the step of forming a film in the interface between air and the mixture of a polymer comprising amine group (—NH) and a compound containing phenol or catechol by exposing the mixture on the air.

To achieve the above object, the present invention provides a method for preparing a double-sided film containing the step of forming a film in the interface between air and the mixture of a polymer comprising amine group (—NH) and a compound containing phenol or catechol by exposing the mixture on the air.

The present invention also provides a double-sided film prepared by exposing the mixture composed of a polymer comprising amine group and a compound containing phenol or catechol on the air.

The present invention further provides a method for preparing a double-sided film containing the step of forming a film in the interface between air and the mixture of a polymer comprising amine group and phenol or catechol, and tyrosinase by exposing the mixture on the air.

In addition, the present invention provides a double-sided film prepared by exposing the mixture of a polymer comprising amine group and phenol or catechol, and tyrosinase on the air.

Advantageous Effect

The present invention relates to a method for preparing a double-sided film containing the step of forming a film in the interface between air and the mixture of a polymer comprising amine group (—NH) and a compound containing phenol or catechol by exposing the mixture on the air. The double-sided film of the present invention is a separation membrane that can separate the interface of liquid phase and gas phase and at the same time can be used as a biomaterial such as a haemostatic and also a waterproof agent. When the film is prepared in a moderate condition by using an enzyme, the film can include proteins and cells, resulting in the multi-functional versatility film that can be useful as a biocatalyst.

BRIEF DESCRIPTION OF THE DRAWINGS

The application of the preferred embodiments of the present invention is best understood with reference to the accompanying drawings, wherein:

FIG. 1 is a diagram illustrating the changes in the interfaces of polyethylenimine (PEI) mixed dopamine (DA), pyrogallol (PA) and pyrocatechol (PC) over the time.

black bar: brightness of the interface between air and the solution; and red bar: brightness of the inner solution

◻: lower face;

DA: dopamine;

NE: norepinephrine;

DHCA: 3,4-dihydroxycinnamic acid; and

PC: pyrocatechol.

Figure 7:
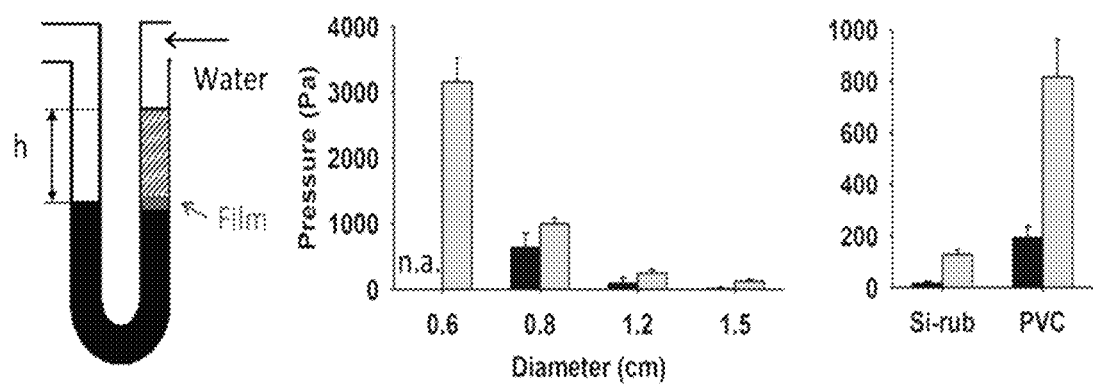

FIG. 7 is a diagram illustrating the adhesive power of the prepared film
  Si-rub: U-shaped tube made of Si-rubber; and
  PVC: U-shaped tube made of polyvinyl chloride (PVC).

Figure 8:
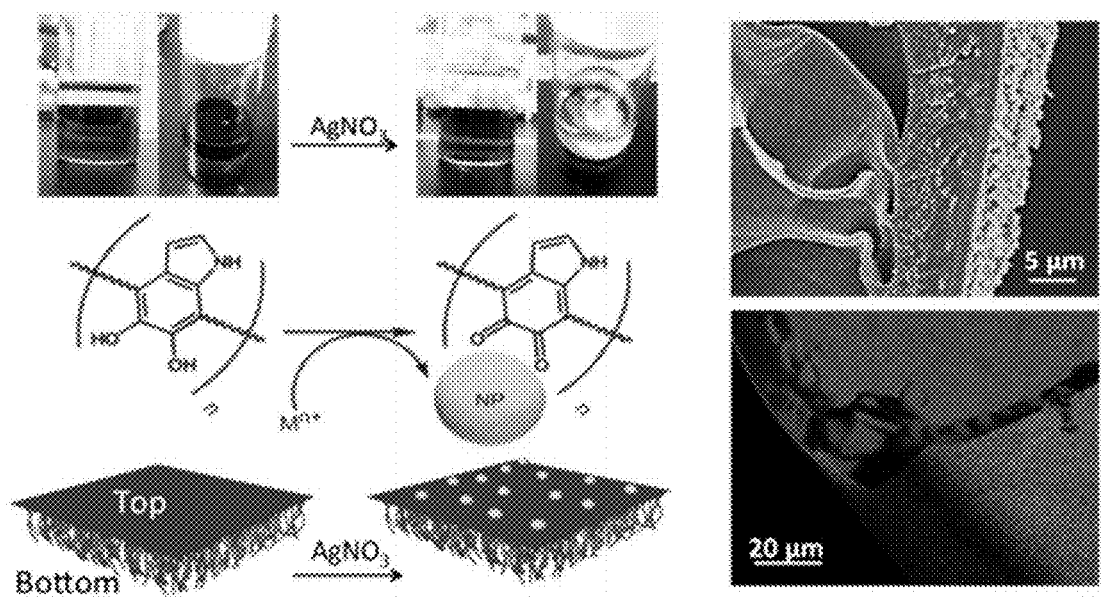

FIG. 8 is a diagram illustrating the fixation of nanoparticles on the film, which is accomplished by adding $AgNO_3$ solution onto the prepared film. The right lower diagram presents the result of element analysis, wherein the purple indicates silver nanoparticles and the red indicates carbon elements.

Figure 9:
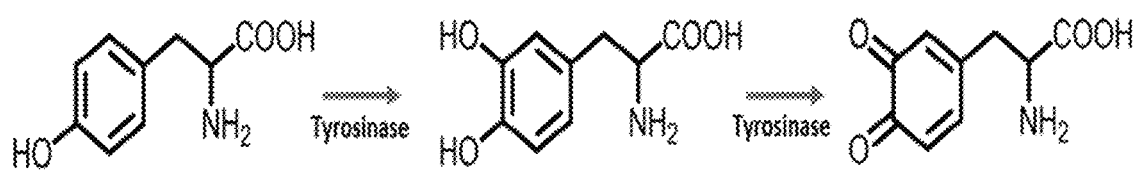

FIG. 9 is a diagram illustrating the oxidation reaction of phenol and catechol mediated by tyrosinase.

Figure 10:
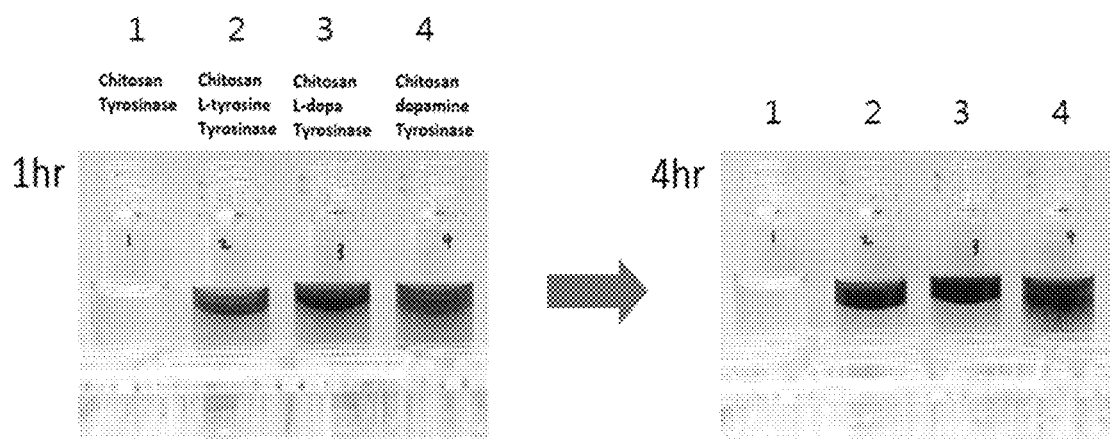

FIG. 10 is a diagram illustrating the result of catechol oxidation of chitosan mixed L-tyrosine, L-dopa, and dopamine mediated by tyrosinase.
  1: chitosan+tyrosinase;
  2: chitosan+L-tyrosine+tyrosinase;
  3: chitosan+L-dopa+tyrosinase; and
  4: chitosan+dopamine+tyrosinase.

Figure 11:
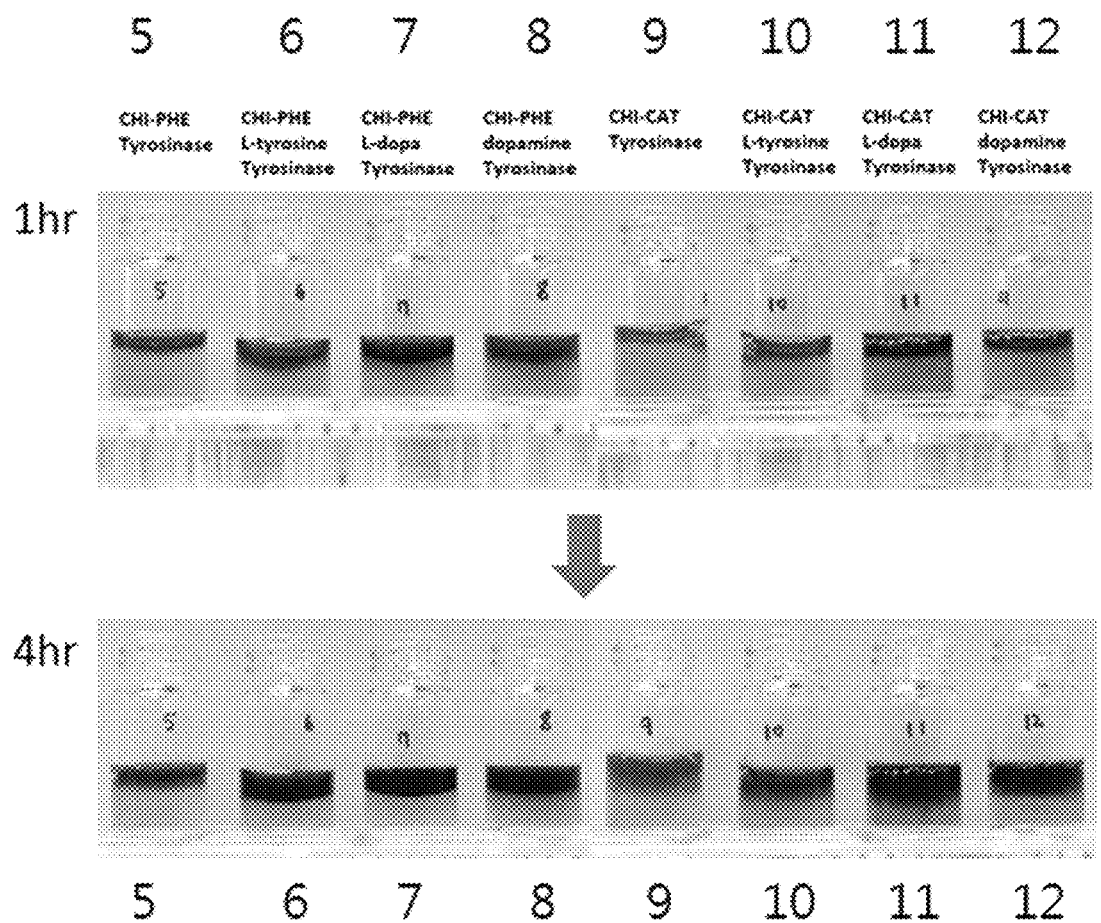

FIG. 11 is a diagram illustrating the result of catechol oxidation of phenol or catechol conjugated chitosan mixed L-tyrosine, L-dopa, and dopamine mediated by tyrosinase.
  CHI-PHE: chitosan+phenol;
  CHI-CAT: chitosan+catechol;
  5: CHI-PHE+tyrosinase;
  6: CHI-PHE+L-tyrosine+tyrosinase;
  7: CHI-PHE+L-dopa+tyrosinase;
  8: CHI-PHE+dopamine+tyrosinase;
  9: CHI-CAT+tyrosinase;
  10: CHI-CAT+L-tyrosine+tyrosinase;
  11: CHI-CAT+L-dopa+tyrosinase; and
  12: CHI-CAT+dopamine+tyrosinase.

FIG. 12 is a diagram illustrating the structural formulas of phenol or catechol-based low molecular compounds such as L-tyrosine, L-dopa, dopamine, norepinephrine, 3,4-dihydroxycinnamic acid (DHCA), and pyrogallol.

Figure 13:
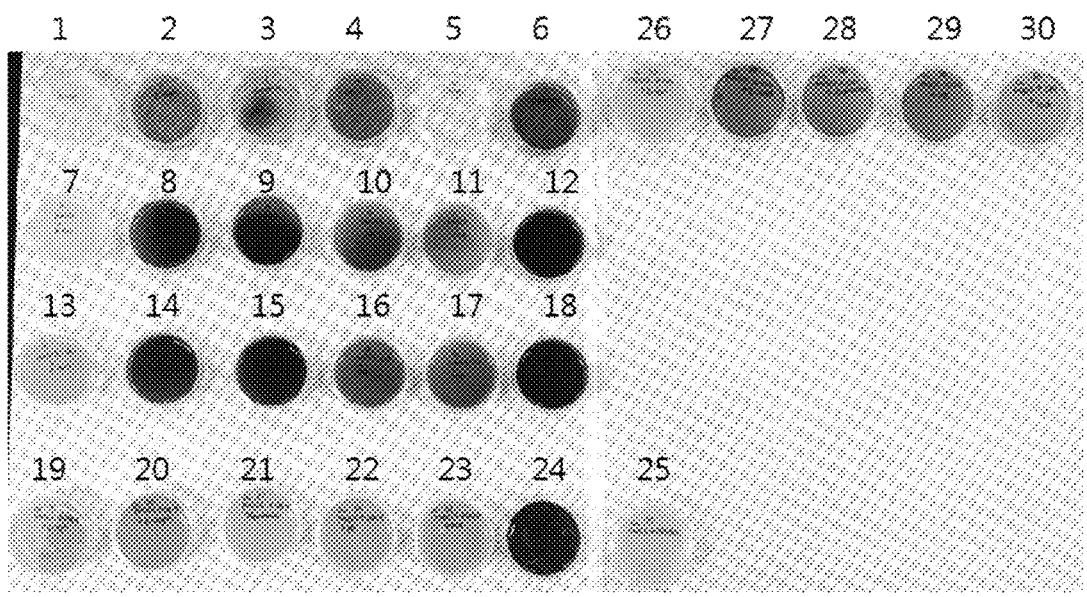

FIG. 13 is a diagram illustrating the film formation by adding phenol or catechol-based low molecular compounds to the mixture composed of the phenol conjugated polymer and the strain secreting tyrosinase.

DESCRIPTION OF THE PREFERRED EMBODIMENTS

Hereinafter, the present invention is described in detail.

The present invention provides a method for preparing a double-sided film containing the step of forming a film in the interface between air and the mixture of a polymer comprising amine group (—NH) and a compound containing phenol or catechol by exposing the mixture on the air.

The present invention also provides a double-sided film prepared by the above method.

The polymer herein is preferably selected from the group consisting of polyacrylamide, polyethylenimine, polyamine, polyamideamine, and chitosan. The compound containing phenol or catechol herein is preferably selected from the group consisting of L-tyrosine, L-dopa, pyrogallol, dopamine, pyrocatechol, norepinephrine, and 3,4-dihydroxycinnamic acid (DHCA).

The mixture herein is preferably prepared by mixing the aqueous solution containing a polymer harboring amine group (10~50 weight part) and the aqueous solution containing a compound harboring phenol or catechol (1~5 weight part) at the ratio of 1:1 (v/v), and more preferably the mixture is prepared by mixing the aqueous solution containing a polymer harboring amine group (10~30 weight part, preferably weight part) and the aqueous solution containing a compound harboring phenol or catechol (1~3 weight part, preferably 2 weight part) at the ratio of 1:1 (v/v)

pH of the said mixture is 5~14. If pH of the liquid mixture is acidic, film would not be formed. So, pH 11 is preferred for the mixture. Herein, the film is generated from the mixture by the difference of oxidation in the interface and in the solution induced by exposing the mixture on the air in the stationary state. Thus, when the mixture is stirred or stays in the state of vacuum, the film is not formed.

The double-sided film of the present invention preferably has different strength and chemical composition on its sides. Such difference can give the both sides of the film different functions. The film can contain proteins or cells.

The preferable method to produce the film is composed of the following steps; amine group of a polymer is reacted with carboxyl group (—COOH) of phenol or catechol and then the film is formed by the difference in catechol oxidation between the interface of the mixture and in the inside of the mixture.

Once the film is formed in the interface between air and the mixture, an aqueous solution containing silver ions is treated thereto. Then, silver nanoparticles are fixed on the surface that has been treated with the aqueous solution containing silver ions. At this time, the aqueous solution containing silver ions can be $AgNO_3$ solution.

It is preferred for silver ions to be converted into silver nanoparticles by oxidation-reduction of catechol for the fixation of silver ions.

It is also preferred to add tyrosinase to the said mixture.

When tyrosinase is added, the condition has to be moderate, for example pH is preferably regulated to be 5~7 and more preferably pH 6. The film can be formed by cross-linking the compound containing phenol or catechol.

To prepare the film of the invention in a preferred embodiment of the present invention, the inventors mixed polyethylenimine (PEI, MW: 750 kDa) 20 wt % solution with 2 wt % solution of either dopamine (DA), pyrogallol (PA), or pyrocatechol (PC) at the ratio of 1:1 (v/v). Each mixture was filled in a container, which stood on the flat board carefully not to be shaken. When pyrogallol (PA) was mixed with PEI, the film was formed in the interface one minute later. When dopamine (DA) or pyrocatechol (PC) was mixed with PEI, the film was formed in the interface 30 minutes later (see FIG. 1).

To compare the catechol oxidation levels, the formed film and the solution included in the inside of the film were examined by UV-Vis. As a result, a lot more catechols were oxidized in the interface than in the solution (see FIG. 2).

To determine the conditions for the film formation, the present inventors regulated pH differently as pH 4, pH 7, and pH 11. Also, under the same pH condition, which was pH 11, other conditions such as stirring, air bubble injection, nitrogen injection, or vacuum condition, etc, were differently tried to observe how they affected the film formation. As a result, the film was formed only at pH 11. When the solution was stirred at pH 11, the interface was well mixed with the solution as a whole, suggesting that there was not much difference in oxidation on both sides, and thus the film was not formed. When air bubble was injected in the inside of the solution, chemical reaction was also evenly induced both in the interface and in the solution, and thus the film was not formed. When nitrogen gas was contacted with the solution or when the mixture was left under vacuum condition, oxidation reaction hardly occurred, neither in the interface nor in the solution itself (see FIG. 3).

The structure of the formed film was investigated by scanning electron microscope (SEM). As a result, the upper face of the film was flat and poreless, and the lower face was stretched longer than the upper face with forming micro-sized channels. The both sides were different not only in the shape but also in chemical composition. On the upper face, catechol functional groups were mainly observed, while on the lower face, polyethylenimine polymers were mainly observed. The whole thickness of the formed film was about 40 uM, among which ⅓ was the thickness of the upper face and ⅔ was the thickness of the lower face (see FIG. 5).

The present inventors also investigated the difference of mechanical strength of both sides of the film caused by the structural difference. As a result, the strength of the upper face was 0.1~0.3 GPa, according to the kinds of catechol, and the strength of the lower face was 0.01~0.03 GPa which was as weak strength as 1/10 of that of the upper face (see FIG. 6).

To measure the maximum pressure of the film, the present inventors generated the film in U-shaped tube for 4 and 24 hours respectively. Then, water was poured on the U-shaped tube and the amount of water spilled until the film was fallen apart from the U-shaped tube was measured. As a result, the pressure that the film prepared via 24-hour reaction could endure in the silicon rubber U-shaped tube of 0.8 cm in diameter was 3000 Pa. As the diameter of the U-shaped tube was bigger, the pressure that the film could endure reduced (see FIG. 7A). The film formed via 24-hour reaction resisted in the silicon rubber (Si-rubber) U-shaped tube of 1.2 cm in diameter until the pressure of 180 Pa, and the pressure was 800 Pa in the polyvinyl chloride (PVC) U-shaped tube (see FIG. 7B).

The present inventors confirmed that when an aqueous solution containing silver ions was added as a secondary solution to the formed film, silver ions were converted into silver nanoparticles by the oxidation/reduction capacity of catechol itself, so that the silver ions could be fixed on the film (see FIG. 8).

To form the film in a moderate condition (pH 6~7) by using an enzyme, the inventors used chitosan as a polymer and added tyrosinase thereto in order to induce oxidation of such molecules that contained phenol and catechol as L-tyrosine, L-dopa, and dopamine.

Therefore, the method for preparing a double-sided film of the present invention is characterized by the procedure that is simple but facilitates the production of a multi-functional versatile film in the interface between air and water via catechol oxidation. The double-sided film prepared by this method is useful as a separation membrane that can separate the interface of the liquid phase and gas phase and at the same time can be used as a biomaterial such as a haemostatic and also a waterproof agent. When the film is prepared in a moderate condition by using an enzyme, the film can include proteins and cells, resulting in the multi-functional versatility film that can be useful as a biocatalyst.

The present invention also provides a method for preparing a double-sided film containing the step of forming a film by exposing the mixture of a polymer containing phenol and tyrosinase on the air.

The present invention also provides a double-sided film prepared by the above method.

The said polymer containing phenol is preferably the complex produced by the reaction between carboxyl group (—COOH) of phenol or catechol and amine group of the polymer. At this time, the polymer is preferably selected from the group consisting of amine group containing polyacrylamide polyethyleneimine, polyamine, polyamideamine, and chitosan.

The mixture can be added with any phenol or catechol low molecule which is exemplified by L-tyrosine, L-dopa, pyrogallol, dopamine, pyrocatechol, norepinephrine, and 3,4-dihydroxycinnamic acid (DHCA). When any of those phenol or catechol-based low molecular compounds is added, a thicker film can be formed.

In a preferred embodiment of the present invention, it was confirmed that when chitosan that was conjugated with phenol or catechol (CHI-PHE or CHI-CAT) was used, a film was successfully formed only with the addition of tyrosinase without the addition of a low molecular compound containing phenol or catechol. At this time, when a low molecular compound containing phenol or catechol was added thereto, a thicker film was formed (see FIGS. 10 and 11).

The present inventors investigated the film formation after the various phenol or catechol-based low molecular compounds such as L-tyrosine, L-dopa, dopamine, norepinephrine, 3,4-dihydroxycinnamic acid (DHCA), and pyrogallol were added to chitosan in the presence of tyrosinase. As a result, it was confirmed that the film was not formed when the polymer was not added. When a low molecular compound containing phenol or catechol was added to chitosan or CHI-PHE, a thicker film was formed (see Table 1 and FIG. 13).

Therefore, the method for preparing a double-sided film of the present invention is a simple method for preparing a multi-functional versatile film that can be generated specifically in the interface between air and water via catechol oxidation. The double-sided film prepared by this method is useful as a separation membrane that can separate the interface of the liquid phase and gas phase and at the same time can be used as a biomaterial such as a haemostatic and also a waterproof agent. When the film is prepared in a moderate condition by using an enzyme, the film can include proteins and cells, resulting in the multi-functional versatility film that can be useful as a biocatalyst.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Film Preparation

The following experiment was performed to prepare the film of the present invention.

Particularly, polyethylenimine (PEI, MW: 750 kDa) 20 wt % solution was mixed with 2 wt % solution of either dopamine (DA), pyrogallol (PA), or pyrocatechol (PC) at the ratio of 1:1 (v/v). Each mixture was filled in a container, which stood on the flat board carefully not to be shaken.

As a result, as shown in FIG. 1, as time went by, the interface between air and the solution turned brown. When pyrogallol (PA) was mixed with PEI, the film was formed in the interface one minute later. When dopamine (DA) or pyrocatechol (PC) was mixed with PEI, the film was formed in the interface and thus the solution was not spilled out but arrested in between the film and the container when observed 30 minutes later (FIG. 1).

Example 2: Investigation of catechol oxidation level of the Interface of the Film and the Inside of the Solution To compare the catechol oxidation level that is a major mechanism for the film formation, the film prepared in Example 1 and the solution included in the film were observed by UV-Vis.

Figure 2:
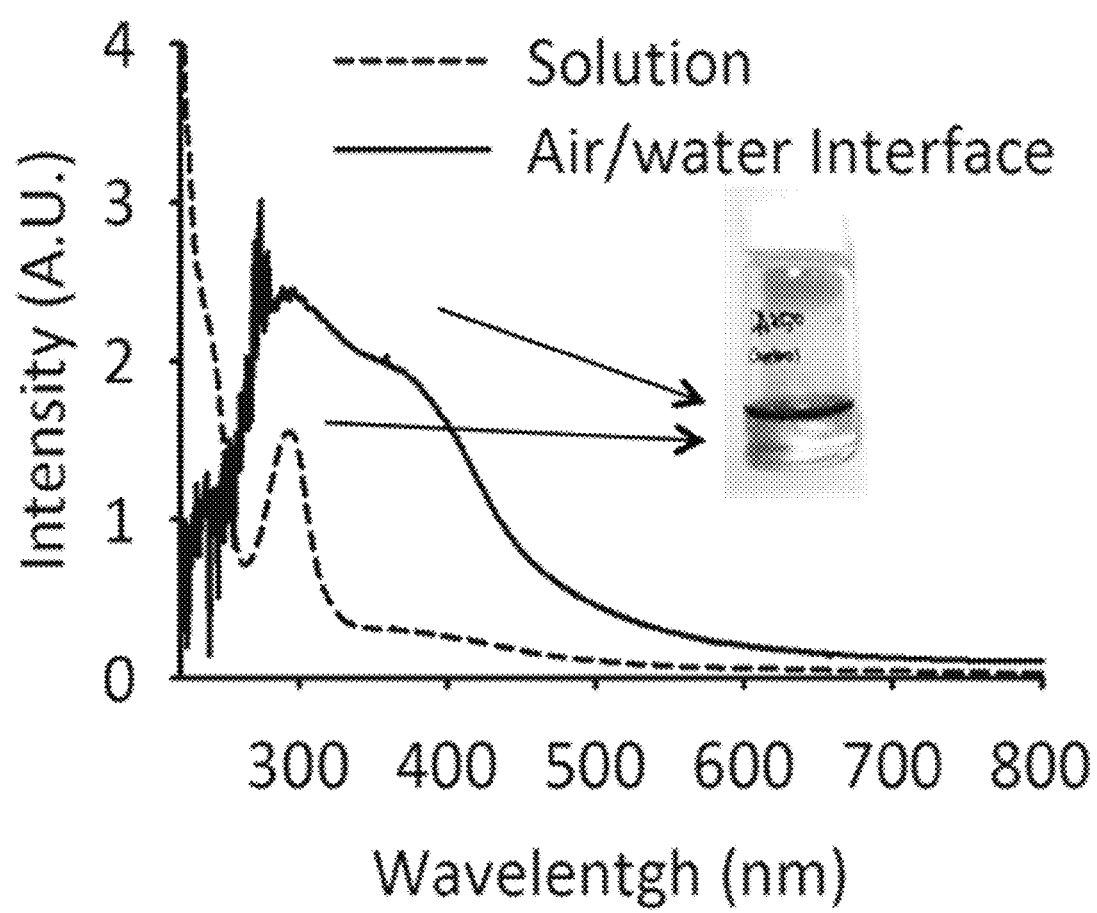
FIG. 2 is a diagram illustrating the absorbance of the film formed in the interface and the solution in the film.

As a result, as shown in FIG. 2, equal peaks were observed at 280 nm (absorbance of the catechol not-oxidized but remained in the solution), and 350~400 nm (absorbance of the oxidized catechol). It was peculiar that absorbance of the catechol itself and absorbance of the oxidized catechol were both very high in the film that had been formed on the interface. When the absorbances were compared, it was confirmed that a lot more catechols were oxidized in the interface than in the solution. The difference in absorbance was also confirmed by the naked eye by observing light yellow solution and dark brown film. The brightness or darkness of color suggested the level of catechol oxidation. So, it can be concluded that the film formation was the same chemical reaction as the reaction of the inside of the solution, but specifically depended significantly on oxidation reaction (FIG. 2).

Example 3: Conditions for Film Formation

The following experiment was performed with regulating various conditions that were believed to be involved in the film formation in order to determine the conditions for the film formation.

Particularly, dopamine (DA) of Example 1 was first used. The solution was contacted with air without being shaken and pH of the solution was regulated differently such as pH 4, pH 7, and pH 11. The interface between water and air was presented as black bar. The red bar indicated the inside of the solution. The film was only formed at pH 11. Under the same pH condition, that was pH 11, other conditions were regulated including stirring, air bubble injection, nitrogen injection, or vacuum condition, etc. Under each condition, the film formation was observed.

Figure 3:
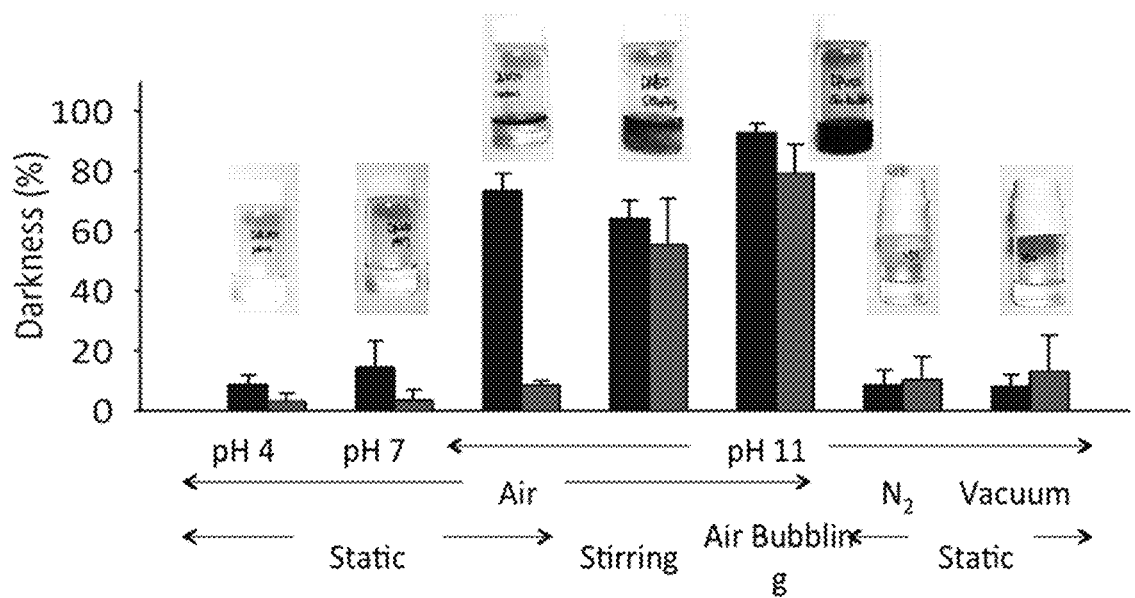
FIG. 3 is a diagram illustrating the formation conditions of the film.

As a result, as shown in FIG. 3, only when the film was formed, the brightness presenting the catechol oxidation level was dark in the interface between water and air, which was consistent with the result of Example 2, and the brightness of the inside of the solution was light. Only when there was a difference in the brightness, that is the catechol oxidation level was different between the interface and the inside of the solution, the film was formed. When the solution was stirred at pH 11, the interface and the solution were mixed as a whole and there was no difference in oxidation level, and accordingly the film was not formed. When air bubble was injected in the inside of the solution, the interface and the solution were also mixed during the air bubble injection, so that chemical reaction was even and regular, resulting in the failure of the film formation. When air bubble was injected, oxidation was accelerated and therefore the interface and the inside of the solution turned dense and dark. From the above observation, it was confirmed that air was an important factor to regulate the oxidation reaction. The solution was contacted with nitrogen gas or maintained in the state of vacuum without being contacted with air. At this time, oxidation reaction was not induced in the interface and not even in the solution itself (FIG. 3).

From the above result, it was concluded that the film was formed by the difference in catechol oxidation between the interface and the inside of the solution and this difference was attributed to such a phenomenon that catechol oxidation was accelerated significantly by the air when the solution was contacted with air.

Example 4: Confirmation of Film Formation by Using Sponge

The solution of Example 1 was absorbed in sponge. The solution absorbed in sponge was not able to contact air like the solution contained in a container. So, oxidization can only occur in the solution smeared in the interface between the sponge and air. To investigate the film formation by using sponge, the polyethylenimine/dopamine solution prepared in Example was absorbed in sponge right after the preparation before oxidation occurred. The excessive solution that remained unabsorbed in sponge was eliminated. The sponge containing the solution was left in the air.

Figure 4:
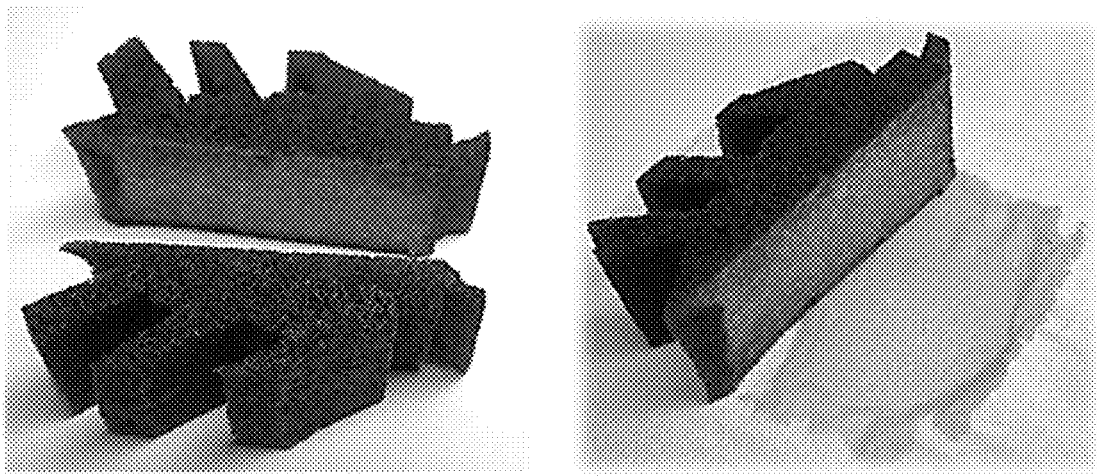
FIG. 4 is a diagram illustrating the difference of catechol oxidation in the inside of the sponge and in the interface.

As a result, as shown in FIG. 4, catechol oxidation was induced outer surface of the sponge that was exposed on the air, consistently with the result of the film formation in Example 1, and thus the color of the outer surface of the sponge turned brown which was getting darker over the time. The sponge that turned brown was cut and the inside of the section was observed. The color of the inside of the sponge was still light yellow which was the same color as the solution, indicating that oxidation was not induced therein (FIG. 4).

Example 5: Microscopic Observation of the Film

To observe the structure of the formed film, the film was observed under scanning electron microscope (SEM).

Particularly, a film was prepared by using dopamine for 30 minutes under the same condition as described in Example 1. The container containing the prepared film was left additionally for 24 hours for further reaction without being shaken until the oxidation reaction was fully induced. Upon completion of the reaction, the film was separated from the solution and then washed with distilled water, followed by freeze-drying. The section of the dried film was observed under scanning electron microscope.

Figure 5:
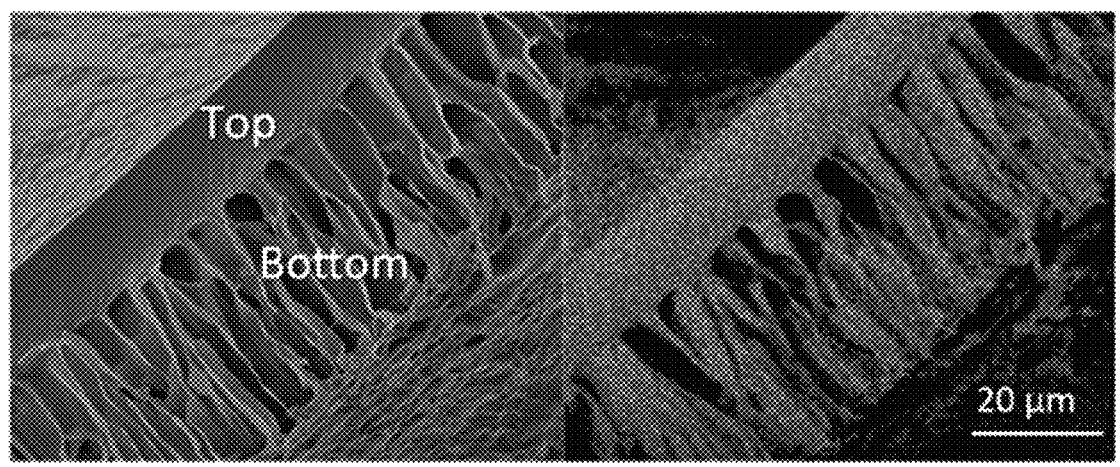
FIG. 5 is a diagram illustrating the section of the prepared film, observed under scanning electron microscope.

As a result, as shown in FIG. 5, the formed film was double sided and the upper face that contacted with air and the lower face that contacted with the solution were different from each other in structure. The upper face of the film was flat and poreless, and the lower face was stretched longer than the upper face with forming micro-sized channels. Other properties of both sides of the film were investigated by energy dispersive x-ray spectrometer (EDS), and the result confirmed that the both sides were different not only in the shape but also in the chemical composition. On the upper face, catechol functional groups were mainly observed, while on the lower face, polyethylenimine polymers were mainly observed. The whole thickness of the formed film was about 40 uM, among which ⅓ was the thickness of the upper face and ⅔ was the thickness of the lower face (FIG. 5).

Example 6: Investigation of the Strength of Both the Upper Face and the Lower Face of the Film To investigate the difference of mechanical strength caused by the structural difference between the upper face of the film and the lower face, the mechanical strength of the film prepared and dried in Example 5 was measured by nano-indentation, atomic force microscope (AFM), and force measurement method.

Figure 6:
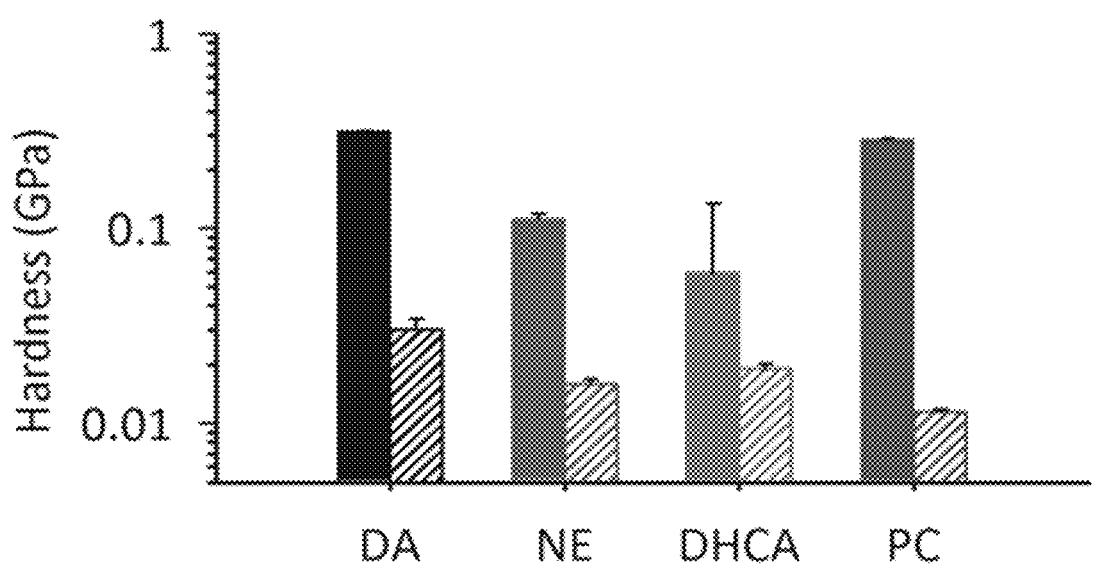
FIG. 6 is a diagram illustrating the strength of the upper face and the lower face of the film ■: upper face.

As a result, as shown in FIG. 6, the strength of the upper face of the dried film was 0.1~0.3 GPa according to the included materials, for example catechol, dopamine (DA), norepinephrine (NE), 3,4-dihydroxycinnamic acid (DHCA), and pyrocatechol (PC). The strongest strength (0.3 GPa) was almost the same as the strength of polystyrene, the well known organic polymer material. In the meantime, the strength of the lower face that contained a plenty of amine polymers and was composed of micro-sized channels was 0.01~0.03 GPa, which was approximately 1/10 of the mechanical strength of the upper face (FIG. 6).

Example 7: Adhesive Power of the Film

The formed film was so tightly adhered on the rim of the container, as mentioned earlier in Example 1, that the solution filling the container was not spilled when the container was up-side-down. At this time, the maximum pressure that the film could hold on was measured by the following experiment.

Particularly, the solution for forming the film using dopamine of Example 1 was loaded in the U-shaped tube made of silicon rubber or polyvinyl chloride (PVC), as illustrated in the left drawing (black) of FIG. 7, followed by reaction for 4 hours and 24 hours to induce the film formation on the mouth of the U-shaped tube which was exposed on the air. The generated film was eliminated from one of the entrances of the U-shaped tube and the other mouth of the U-shaped tube was only sealed with the generated film as shown in the left drawing of FIG. 7. On the film that covering one entrance of the U-shaped tube was poured water as shown in the left drawing (gray) of FIG. 7 and the amount of water spilled thereon until the film was torn apart from the tube was measured. Precisely, the weight of water per unit area that pressed the film until the film was torn apart was calculated and converted into pressure.

As a result, as shown in FIG. 7, the pressure that the film prepared via 24-hour reaction could endure in the silicon rubber U-shaped tube of 0.8 cm in diameter was 3000 Pa. As the diameter of the U-shaped tube was increased, the pressure that the film could hold was decreased (FIG. 7A). The film was adhered on the rim only and the center part of the film was just suspended on water, that was the solution, so that when the diameter of the tube was increased, the center of the film was torn but not the film that sealed rim area. The pressure that the film could hold differed from the kinds of material of the U-shaped tube if the tubes were in the same diameter. For example when the silicon rubber (Si-rubber) U-shaped tube of 1.2 cm in diameter was sealed with the film that was formed by 24 hour reaction, the film was still preserved as unbroken up to the pressure of 180 Pa. In the meantime, the film formed on the polyvinyl chloride (PVC) U-shaped tube could hold on up to the pressure of 800 Pa (FIG. 7B).

Example 8: Preparation of Method for Preparing Janus Organic/Inorganic Hybrid Film on the Film When the film was formed on the tube, indicating that the film sealed the tube and prevented the solution from being spilled out, a secondary solution can be added on the film. The two solutions were not mixed because there was the film in the middle to prevent them from being mixed and the film was not moved. In this experiment, an aqueous solution containing silver ions was used as the secondary solution. When the secondary solution was added, the silver ions in the secondary solution were converted into silver nanoparticles by the oxidation/reduction capacity of catechol itself, which were then fixed on the film.

Particularly, as shown in Example 1, the film was formed in the interface between air and the solution via 4-hour reaction using dopamine and polyethylenimine. Without removing the solution under the film, 25 mM AgNO$_3$ solution was added onto the film in order to cover all the space of the film. The film was then left for 5 minutes, during which silver ions were reduced and fixed thereon. 5 minutes later, the whole solution was eliminated and the film was apart from the tube and washed with distilled water, followed by freeze-drying. The formation of silver nanoparticles was observed under scanning electron microscope.

As a result, as shown in FIG. 8, reduction and fixation of silver ions were faster than the diffusion velocity of the ions to pass through the film. So, silver nanoparticles were formed only on the upper face where the silver ion solution was directly contacted, by which the color of the upper face turned gray with gloss. The fixation of silver nanoparticles on the upper face was confirmed by SEM. Element analysis also confirmed the overall fixation of silver nanoparticles (purple) on the upper face (FIG. 8).

Example 9: Preparation of the Film Under Moderate Condition by Using an Enzyme

The film formation in the above example was achieved at pH 11 and mediated by oxidation of catechol molecules. However, in this method, pH was too high and the solution contained polyethylenimine, the polymer, suggesting that these conditions can affect the protein activity and cell survival. Therefore, in order to introduce proteins and cells into the film, a method to generate the film under more moderate condition with a safer polymer was studied.

Particularly, as an alternate polymer, chitosan that has been widely used as a biomaterial, was used. A film was prepared in a rather mild condition at pH 6~7 with the polymer by oxidation of L-tyrosine, L-dopa, and dopamine, which were the molecules containing phenol and catechol using an enzyme. The enzyme used at this time was tyrosinase, which was the most important enzyme for the biosynthesis of melanin pigment and found in a various living things including plants, microorganisms, and animal cells. Tyrosinase oxidizes monophenol group of tyrosine to produce dopa. It also oxidizes catechol group of dopa to produce dopaquinone (FIG. 9). Chitosan was dissolved in 1×PBS (pH 7.4, 10 mg/ml). The oxygen remaining in the solution was eliminated by using a sonicator. L-tyrosine was dissolved in distilled water at the concentration of 1 mg/ml. L-dopa and dopamine were dissolved in distilled water at the concentration of 5 mg/ml. Tyrosinase that had been extracted from mushroom was purchased from Sigma-Aldrich, which was then dissolved in distilled water at the concentration of 500 U/ml.

The reaction solution for the formation of the film was composed of chitosan solution, phenol/catechol containing low molecular compound, and tyrosinase at the ratio of 3:1:1. The reaction of the reaction mixture was induced at room temperature and 1~4 hours later the film formation was observed.

Tyrosinase was added to phenol-conjugated chitosan (CHI-PHE) or catechol-conjugated chitosan (CHI-CAT), followed by experiment by the same manner as described in the above. CHI-PHE and CHI-CAT were dissolved in 1×PBS (pH 7.4). For the synthesis of CHI-PHE and CHI-CAT, phenol was conjugated to the backbone of chitosan by using the standard EDC (1-ethyl-3-(3-dimethylamino propyl)carbodiimide) chemical method. Particularly, chitosan was first dissolved in 0.1 M HCl solution. pH was slowly increased to 5.5 by using 5 M NaOH in order to induce the optimum EDC coupling reaction. 3-(4-hydroxyphenyl)propionic acid and 3,4-dihydroxycinnamic acid (DHCA) dissolved in distilled water, and EDC dissolved in ethanol were slowly added to the solution containing chitosan. The reaction mixture was stirred vigorously at room temperature for 12 hours. pH of the reaction mixture was monitored. After 12 hours of reaction, dialysis of the reaction mixture was performed first in the oxidized distilled water for 24 hours and then in another distilled water for 24 hours (MWCO: 3500, Spectrapor, USA). The final product was freeze-dried and stored in a humid-free desiccator until the next experiment. The degree of substitution of phenol was determined by measuring $OD_{280}$ by UV-vis spectrophotometry considering the content of phenol. 3-(p-hydroxyphenyl)propionic acid standard solution was used to produce the standard curve of phenol concentration and phenol was quantified thereafter. The degree of substitution of phenol in the backbone of chitosan was 9.0%, calculated by UV-vis spectrophotometry. The phenol conjugation onto CHI-PHE was 9% and catechol conjugation onto CHI-CAT was 10.5%. 1~4 hours later, the film formation was observed.

10 mg/ml of a polymer (CHI/CHI-PHE/CHI-CAT), 500 U/ml of tyrosinase, and a lower molecular material (l-tyrosine 1 mg/ml, l-DOPA 5 mg/ml, or dopamine 5 mg/ml) were mixed at the ratio of 3:1:1, followed by reaction. For the condition without the lower molecular material, 1x PBS was added instead of the lower molecular material.

As a result, as shown in FIGS. 10 and 11, tyrosinase induced oxidation of catechol containing molecules, so that the enzyme mediated the film formation in the interface between water and air in a moderate condition. The reason of the film formation in the interface under the above condition was so called oxygen contact. Tyrosinase needs oxygen in order to oxidize phenol and catechol and when the oxidized molecules are contacted with oxygen, the oxidation of the molecules is accelerated, resulting in the formation of the film in the interface (FIG. 10).

The film was also formed with phenol-conjugated or catechol-conjugated chitosan under the same condition as described in the above even without a molecule containing phenol or catechol but if an enzyme was added. When a molecule containing phenol or catechol was added, the formed film was thicker (FIG. 11).

Example 11: Film Formation with the Addition of Phenolic/Catecholic Small Molecule In the course of producing a film using tyrosinase, various phenol/catecholic small molecules were added to chitosan.

Particularly, 2.5 ml of chitosan or phenol-conjugated chitosan (CHI-PHE) was used as a polymer. As a phenol/catecholic small molecule, 500 µl of each mg/ml L-tyrosine, L-dopa, dopamine, norepinephrine, 3,4-dihydroxycinnamic acid (DHCA), and pyrogallol shown in FIG. 12 was added. The strain expressing tyrosinase was cultured in Cu free medium (7~12 of Table 1) or in Cu containing medium (13~31 of Table 1), which was added thereto (2.5 ml). As the normal control (1~6 of Table 1), 500 µl of 10 mg/ml phenol/catecholic small molecule solution was added to 5 ml of 1×PBS.

As a result, as shown in Table 1 and FIG. 13, when the polymer was not added, the film was not formed. When the phenol/catecholic small molecule was added to chitosan or phenol-conjugated chitosan, the thickness of the film generated thereby was increased (Table 1 and FIG. 13).

TABLE 1

Condition for film formation

| | phenol/catecholic small molecule | Polymer | Enzyme | Film thickness |
|---|---|---|---|---|
| 1 | L-tyrosine | — | 1X PBS | X |
| 2 | L-dopa | — | 1X PBS | X |
| 3 | dopamine | — | 1X PBS | X |
| 4 | norepinephrine | — | 1X PBS | X |
| 5 | DHCA | — | 1X PBS | X |
| 6 | pyrogallol | — | 1X PBS | X |
| 7 | L-tyrosine | — | tyrosinase | X |
| 8 | L-도파 | — | tyrosinase | X |
| 9 | dopamine | — | tyrosinase | X |
| 10 | norepinephrine | — | tyrosinase | X |
| 11 | DHCA | — | tyrosinase | X |
| 12 | pyrogallol | — | tyrosinase | X |
| 13 | L-tyrosine | — | tyrosinase (Cu) | X |
| 14 | L-dopa | — | tyrosinase (Cu) | X |
| 15 | dopamine | — | tyrosinase (Cu) | X |
| 16 | norepinephrine | — | tyrosinase (Cu) | X |
| 17 | DHCA | — | tyrosinase (Cu) | X |
| 18 | pyrogallol | — | tyrosinase (Cu) | X |
| 19 | L-tyrosine | CHI-PHE | tyrosinase (Cu) | Thin |
| 20 | L-dopa | CHI-PHE | tyrosinase (Cu) | Intermediate |
| 21 | dopamine | CHI-PHE | tyrosinase (Cu) | Intermediate |
| 22 | norepinephrine | CHI-PHE | tyrosinase (Cu) | Intermediate |
| 23 | DHCA | CHI-PHE | tyrosinase (Cu) | Thin |
| 24 | pyrogallol | CHI-PHE | tyrosinase (Cu) | Thick |
| 25 | — | CHI-PHE | tyrosinase (Cu) | Thin |
| 26 | L-tyrosine | chitosan | tyrosinase (Cu) | Thin |
| 27 | L-dopa | chitosan | tyrosinase (Cu) | Intermediate |
| 28 | dopamine | chitosan | tyrosinase (Cu) | Intermediate |
| 29 | norepinephrine | chitosan | tyrosinase (Cu) | Intermediate |
| 30 | DHCA | chitosan | tyrosinase (Cu) | Thin |
| 31 | pyrogallol | chitosan | tyrosinase (Cu) | Thick |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preparing a double-sided film comprising:
   (a) mixing a polymer comprising an amine group (—NH) and a compound comprising a phenol or catechol group to form a mixture; and
   (b) exposing the mixture to air to form the double-sided film in an interface between the air and the mixture, wherein the film is formed by a difference of catechol oxidation between the interface and an interior of the mixture.

2. The method for preparing a double-sided film according to claim 1, wherein the polymer is selected from the group consisting of polyacrylamide, polyethylenimine, polyamine, polyamideamine, and chitosan.

3. The method for preparing a double-sided film according to claim 1, wherein the compound comprising the phenol or catechol group is selected from the group consisting of L-tyrosine, L-dopa, pyrogallol, dopamine, pyrocatechol, norepinephrine, and 3,4-dihydroxycinnamic acid (DHCA).

4. The method for preparing a double-sided film according to claim 1, wherein the mixture is prepared by mixing an aqueous solution comprising a polymer comprising an amine group (10~50 weight part) and an aqueous solution comprising a compound comprising a phenol or catechol group (1~5 weight part) at a volume ratio of 1:1.

5. The method for preparing a double-sided film according to claim 1, wherein the pH of the mixture is 5~14.

6. The method for preparing a double-sided film according to claim 1, wherein the both sides of the double-sided film have different strength and chemical composition from each other.

7. The method for preparing a double-sided film according to claim 1, further comprising fixing silver nanoparticles by treating an aqueous solution containing silver ions after forming the film in the interface between air and the mixture.

8. The method for preparing a double-sided film according to claim 7, wherein the silver ions were reduced into silver nanoparticles by the oxidation/reduction of catechol, so that the silver ions were fixed on the film.

9. The method for preparing a double-sided film according to claim 1, wherein the mixture further comprises tyrosinase.

10. A double-sided film prepared by a method of:
(a) mixing a polymer comprising an amine group and a compound comprising a phenol or catechol group to form a mixture; and
(b) exposing the mixture to air to form the double-sided film in an interface between the air and the mixture,
wherein the film is formed by a difference of catechol oxidation between the interface and an interior of the mixture.

11. A method for preparing a double-sided film, comprising forming a film by exposing a mixture of a polymer comprising a phenol group and tyrosinase to air.

12. The method for preparing a double-sided film according to claim 11, wherein the mixture further comprises a compound comprising a phenol or catechol group.

13. A double-sided film prepared by exposing a mixture of a compound comprising a phenol group and tyrosinase to air.

* * * * *